US012628787B2

(12) United States Patent
Prenveille

(10) Patent No.: US 12,628,787 B2
(45) Date of Patent: May 19, 2026

(54) PEPPER VARIETY NUN 70064 PPH

(71) Applicant: Nunhems B.V., Nunhem (NL)

(72) Inventor: Baptiste Andre Emile Prenveille, Culiacan (MX)

(73) Assignee: Nunhems B.V., Nunhem (NL)

( * ) Notice: Subject to any disclaimer, the term of this patent is extended or adjusted under 35 U.S.C. 154(b) by 315 days.

(21) Appl. No.: 18/320,736

(22) Filed: May 19, 2023

(65) Prior Publication Data

US 2023/0371458 A1 Nov. 23, 2023

Related U.S. Application Data

(60) Provisional application No. 63/343,868, filed on May 19, 2022.

(51) Int. Cl.
A01H 5/10 (2018.01)
A01H 5/08 (2018.01)
A01H 6/82 (2018.01)

(52) U.S. Cl.
CPC .............. A01H 6/822 (2018.05); A01H 5/08 (2013.01); A01H 5/10 (2013.01)

(58) Field of Classification Search
CPC .................................. A01H 5/10; A01H 6/822
See application file for complete search history.

(56) References Cited

U.S. PATENT DOCUMENTS

| | | | |
|---|---|---|---|
| 8,492,619 B2 | 7/2013 | Bar et al. | |
| 2006/0037100 A1 | 2/2006 | Kim et al. | |
| 2015/0126380 A1 | 5/2015 | Van Dun | |
| 2015/0245570 A1 | 9/2015 | Vogelaar et al. | |
| 2019/0357492 A1* | 11/2019 | Baek ...................... | A01H 6/822 |

OTHER PUBLICATIONS

Haun et al., 2011, The Composition and Origins of Genomic Variation among Individuals of the Soybean Reference Cultivar Williams 82, Plant Physiology 155: 645-655. (Year: 2011).*
Großkinsky et al., 2015, Plant phenomics and the need for physiological phenotyping across scales to narrow the genotype-to-phenotype knowledge gap, Journal of Experimental Botany 66(18): 5429-5440. (Year: 2015).*
Applying for a Plant Variety Certificate of Protection by the USDA reference to Exhibit A; accessed May 1, 2023. (Year: 2023).*
UPOV EDV Explanatory Notes 14 and 30; Apr. 6, 2017. (Year: 2017).*
Poehlman et al. (Poehlman et al., 1995, Methods in Plant Breeding IV, Iowa State Press, pp. 1-494, selected pp. 157, 159-180 only. (Year: 1995).*
Barbara Pleasant, How to Grow Peppers in Containers, GrowVeg, published Jun. 9, 2016, available at https://www.growveg.com/guides/how-to-grow-peppers-in-containers/, last accessed May 7, 2021. (Year: 1996).*

"Bell and Chile Peppers", Presented by FDA—Western Institute for Food Safety & Security, pp. 1-7, 2016. URL—https://www.wifss.ucdavis.edu/wp-content/uploads/2016/10/Peppers_PDF.pdf.
"Calibration Book-Sweet Pepper, Hot Pepper, Paprika, Chili", Naktuinbouw Calibration Book, *Capsicum annuum* L.—Sweet Pepper, Hot Pepper, Paprika, Chili, Version 1, Dec. 2010, 88 pages.
"Sweet Pepper, Hot Pepper, Paprika, Chili, UPOV Code: Capsi_Ann, (*Capsicum annuum* L.)", Guidelines for the conduct of tests for distinctness, uniformity and stability, UPOV, International Union for the Protection of New Varieties of Plants, Geneva, TG/76/8, Apr. 5, 2006, 48 pages. URL—https://www.upov.int/edocs/tgdocs/en/tg076_08.pdf.
"Sweet Pepper, Hot Pepper, Paprika, Chili, UPOV Code: Capsi_Ann, (*Capsicum annuum* L.)", Guidelines for the conduct of tests for distinctness, uniformity and stability, UPOV, International Union for the Protection of New Varieties of Plants, Geneva, TG/76/8, Rev. 2, Sep. 20, 2018, 52 pages. URL—https://www.upov.int/edocs/tgdocs/en/tg076. pdf.
"Application for Plant Variety Protection Certificate", US Department of Agriculture, Agricultural Marketing Service, Science and Technology Program, Plant Variety Protection Office, Form ST 470, Jan. 31, 2022, 9 pages.
"Objective description of Variety: Pepper (*Capsicum* spp.)", US Department of Agriculture, Agricultural Marketing Service, Science and Technology, Plant Variety Protection Office, Exhibit C, Jun. 2015, 4 pages.
Hartz, et al., "Bell Pepper Production in California" University of California Division of Agriculture and Natural Resources—Vegetable Production Series, Publication 7217, pp. 1-4. Feb. 1, 2008. URL—https://escholarship.org/ content/qt43t2v37n/qt43t2v37n.pdf.
Ince, et al., "Genetic relationships within and between *Capsicum* species", Biochemical genetics, vol. 48, Nov. 15, 2009, pp. 83-95.
Kim, et al., "Callus growth and plant regeneration in diverse cultivars of cucumber (*Cucumis sativus* L.)", Plant Cell, Tissue and Organ Culture, vol. 12, Mar. 1998, pp. 67-74.
Kothari, et al., "Chilli peppers—a review on tissue culture and transgenesis", Biotechnology advances, vol. 28, Issue 1, Jan.-Feb. 2010, pp. 35-48.
Martin, et al., "Identification of markers linked to agronomic traits in globe artichoke", Australian Journal of Crop Science, vol. 1, Issue 2, 2008, pp. 43-46.
Needleman, et al., "A general method applicable to the search for similarities in the amino acid sequence of two proteins", Journal of Molecular Biology, vol. 48, Issue 3, 1970, pp. 443-453.
Nikolova, et al., "Diploidization of cucumber (*Cucumis sativus* L.) haploids by colchicine treatment", Acta Societas Botanicorum Poloniae, vol. 65, Issues 3-4, 1996, pp. 311-317.
Rice, et al., "EMBOSS: The European Molecular Biology Open Software Suite", Trends in Genetics, vol. 16, Issue 6, Jun. 1, 2000, pp. 276-277.
Robert W. Allard, "Principles of Plant Breeding", Second edition, 1999, pp. 64-67.

(Continued)

*Primary Examiner* — Bratislav Stankovic
(74) *Attorney, Agent, or Firm* — ArentFox Schiff LLP

(57) ABSTRACT

A new and distinct pepper variety NUN 70064 PPH is disclosed, as well as seeds and plants and heads or leaves thereof.

27 Claims, 1 Drawing Sheet

(56) References Cited

OTHER PUBLICATIONS

Songstad, et al., "Genome Editing of Plants", Critical Reviews in Plant Sciences, vol. 36, Issue 1, 2017, pp. 1-23.

Tiwari, et al., "Parthenocarpic potential in *Capsicum annuum*L. is enhanced by carpelloid structures and controlled by a single recessive gene", BMC Plant Biology, vol. 11, Issue 1, Article No. 143, Oct. 21, 2011, pp. 2-14.

Vos, et al., "AFLP: a new technique for DNA fingerprinting", Nucleic acids research, vol. 23, Issue 21, Jan. 1, 1995, pp. 4407-4414.

Wijnker, et al., "Hybrid recreation by reverse breeding in *Arabidopsis thaliana*", Nature Protocols, vol. 9, Issue 4, Mar. 6, 2014, pp. 761-772.

* cited by examiner

PEPPER VARIETY NUN 70064 PPH

CROSS-REFERENCE TO RELATED APPLICATION

This application claims priority of the U.S. Provisional Application No. 63/343,868 filed on May 19, 2022, which is hereby incorporated by reference in its entirety.

FIELD OF DISCLOSURE

The disclosure relates to the field of plant breeding and, more specifically, to the pepper variety NUN 70064 PPH. The disclosure further relates to vegetative reproductions of pepper variety NUN 70064 PPH, methods for tissue culture of pepper variety NUN 70064 PPH, and methods for regenerating a plant from such a tissue culture and also to phenotypic variants of pepper variety NUN 70064 PPH. The disclosure also relates to progeny of pepper variety NUN 70064 PPH and the hybrid varieties obtained by crossing pepper variety NUN 70064 PPH as a parent line with plants of other varieties or parents lines.

BACKGROUND OF THE DISCLOSURE

The goal of plant breeding is to combine various desirable traits in a single variety. Such desirable traits may include greater yield, resistance to diseases, insects or other pests, tolerance to heat and drought, better agronomic quality, higher nutritional value, enhanced growth rate, and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype. Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

One crop species that has been subject to such breeding programs and is of particular value is the pepper. Pepper (*Capsicum* spp.) is naturally a diploid and the basic chromosome number of the genus is x=12, most are 2n=2x=24, including the cultivated ones. A few wild species have 2n=26. Ploidy changes (both tetraploidy and haploidy) are relatively easy to induce in *Capsicum* species. Doubled haploids have proved particularly valuable in the analysis of the genetically complex basis of some resistances to pests and diseases.

The genus *Capsicum* originated in American tropics. The fruit of most species of *Capsicum* produce a strong burning sensation (pungency or spiciness) in the mouth of the unaccustomed eater due to the presence of capsaicin (methyl vanillyl nonanamide), a lipophilic chemical, making it as an important spice commodity. Capsaicin can be present in large quantities in the placental tissue (which holds the seeds), the internal membranes, and to a lesser extent, the other fleshy parts of the fruits of plants in this genus. The seeds themselves do not produce any capsaicin. The amount of capsaicin in the fruit is highly variable and dependent on genetics and environment, giving almost all types of *Capsicum* varied amounts of perceived heat.

The most recognizable *Capsicum* without capsaicin is the bell pepper, a cultivar of *Capsicum annuum*, which has a zero rating on the Scoville scale. The lack of capsaicin in bell peppers is due to a recessive gene that eliminates capsaicin and, consequently, the "hot" taste usually associated with the rest of the *Capsicum* family.

Pepper can be classified according to its target market: fresh market and processing peppers. Peppers for the fresh market require that the fruits are firm, shiny and have fresh green calyx and stem. They are typically consumed fresh as a snack or used in salad or sandwiches or as a cooked vegetable. On the other hand, processing peppers are used for freezing or dehydrating and can be dried, ground as spices and processed, e.g., pickled, canned, brined or in salsas.

In the United States, majority of the peppers produced is the bell pepper (i.e., sweet pepper), which are mainly marketed fresh. California and Florida are the lead producers of bell peppers. Bell peppers are available year-round with supply at the greatest volume from May to July and March to April in California and Florida, respectively. Bulk of the bell peppers grown and harvested are green, but premium is given to colored bell peppers (i.e., red, yellow).

Both hybrids and open-pollinated varieties are used for production in the United States, with a growing trend in the use of seeded hybrid varieties. Hybrid varieties offer the advantages of easy combination of dominant and recessive traits, such as disease resistance, from a set of inbred parents, as well as careful control of parentage.

Advances in biotechnology have also resulted in genetically engineered pepper plants with improved traits. For example, fungal resistant pepper plants comprising a Pep-EST or PepDef gene where the expression of the nucleic acid sequence in the plant resulted in increased resistance to fungal infection, see, e.g., U.S. Pub. No. 2006/0037100, which hereby incorporated by reference in its entirety.

While breeding efforts to date have provided a number of useful pepper varieties with beneficial traits, there remains a great need in the art for new varieties with further improved traits. Such plants would benefit farmers and consumers alike by improving crop yields and/or quality. Breeding objectives include resistance to pests and diseases, improvement of fruit quality, protection against biotic and abiotic stresses, varying the color, texture and flavor of the fruit, optimizing flesh thickness, yield, suitability to various climatic circumstances, heat, solid content (% dry matter), or sugar content.

SUMMARY OF VARIOUS ASPECTS OF THE DISCLOSURE

The disclosure provides for a pepper variety NUN 70064 PPH, products thereof, and methods of using the same. NUN 70064 PPH is a jalapeno pepper variety for the fresh market and is suitable for growing in the open field.

The disclosure also provides a pepper plant, or part thereof, having all of the physiological and morphological characteristics of pepper variety NUN 70064 PPH when grown under the same environmental conditions.

In another aspect, pepper variety NUN 70064 PPH or a progeny thereof comprises resistance to Tomato Spotted Wilt Virus (TSWV), measured according to UPOV standards described in TG/76/8.

The disclosure also provides for a progeny of pepper variety NUN 70064 PPH. In another aspect, the disclosure provides a plant or a progeny retaining all or all but one, two, or three of the "distinguishing characteristics" or all or all but one, two, or three of the "morphological and physiological characteristics" of pepper variety NUN 70064 PPH and methods for producing that plant or progeny.

In one aspect, the disclosure provides a plant or a progeny having all the physiological and morphological characteristics of variety NUN 70064 PPH when grown under the same environmental conditions. In another aspect, the plant or progeny has all or all but one, two, or three of the physiological and morphological characteristics of pepper variety NUN 70064 PPH when measured under the same environmental conditions and e.g., evaluated at significance levels of 1%, 5% or 10% significance (which can also be expressed as a p-value) for quantitative characteristics and determined by type or degree for non-quantitative characteristics, wherein a representative sample of seed of pepper variety NUN 70064 PPH has been deposited under Accession Number NCIMB 44718. In another aspect, the plant or progeny has all or all but one, two or three of the physiological and morphological characteristics as listed in Table 1 for pepper variety NUN 70064 PPH when measured under the same environmental conditions and e.g., evaluated at significance levels of 1%, 5% or 10% significance (which can also be expressed as a p-value) for quantitative characteristics and determined by type or degree for non-quantitative characteristics.

In one aspect, the disclosure provides, a seed of pepper variety NUN 70064 PPH, wherein a representative sample of said seed has been deposited under Accession Number NCIMB 44718. The disclosure also provides for a plurality of seeds of pepper variety NUN 70064 PPH. The seed of pepper variety NUN 70064 PPH may be provided as an essentially homogeneous population of pepper seed. The population of seed of pepper variety NUN 70064 PPH may be particularly defined as being essentially free from other seed. The seed population may be grown into plants to provide an essentially homogeneous population of pepper plants as described herein.

The disclosure also provides a plant grown from a seed of pepper variety NUN 70064 PPH and a plant part thereof.

The disclosure furthermore provides a pepper fruit produced on a plant grown from a seed of pepper variety NUN 70064 PPH.

In another aspect, the disclosure provides, a seed growing or grown on a plant of variety NUN 70064 PPH (i.e., produced after pollination of the flower of pepper variety NUN 70064 PPH).

In another aspect, the disclosure provides for a hybrid variety of pepper called NUN 70064 PPH.

In another aspect, the disclosure provides for a plant part obtained from variety NUN 70064 PPH, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, a cotyledon, a scion, a stock, a rootstock, a pistil, an anther, or a flower or a part thereof. Fruits are particularly important plant parts. In a further aspect, the plant part obtained from variety NUN 70064 PPH is a cell, optionally a cell in a cell or tissue culture. That cell may be grown into a plant of variety NUN 70064 PPH.

The disclosure also provides a cell culture of pepper variety NUN 70064 PPH, and a plant regenerated from pepper variety NUN 70064 PPH, wherein said plant has all the characteristics of pepper variety NUN 70064 PPH when grown under the same environmental conditions, as well as methods for culturing and regenerating pepper variety NUN 70064 PPH. Alternatively, a regenerated plant may have one characteristic that is different from pepper variety NUN 70064 PPH, and which otherwise has all of the physiological and morphological characteristics of pepper variety NUN 70064 PPH.

The disclosure further provides a vegetatively propagated plant of variety NUN 70064 PPH having all or all but one, two, or three of the morphological and physiological characteristics pepper variety NUN 70064 PPH when grown under the same environmental conditions.

In another aspect, the disclosure provides a method of producing a pepper plant comprising crossing pepper variety NUN 70064 PPH with itself or with another pepper variety and selecting a progeny pepper plant from said crossing.

The disclosure also provides a method of producing a pepper plant derived from pepper variety NUN 70064 PPH.

In a further aspect, the disclosure provides a method of producing a hybrid pepper seed comprising crossing a first parent pepper plant with a second parent pepper plant and harvesting the resultant hybrid pepper seed, wherein said first pepper plant or second pepper plant is pepper variety NUN 70064 PPH. Also provided is a hybrid pepper plant produced from crossing a first pepper plant and second pepper plant and harvesting the resultant hybrid pepper seed, wherein said first pepper plant or second pepper plant is pepper variety NUN 70064 PPH. Moreover, the hybrid pepper plant grown from the hybrid pepper seed is provided.

In another aspect, the disclosure provides a method of introducing a single locus conversion into the plant of variety NUN 70064 PPH, wherein a representative sample of seed of said pepper variety has been deposited under Accession Number NCIMB 44718, wherein the plant comprises the single locus conversion and otherwise has all of the physiological and morphological characteristics of the plant of pepper variety NUN 70064 PPH.

In yet another aspect, the disclosure provides a method for introducing a desired trait into pepper variety NUN 70064 PPH, said method comprises transforming the plant of pepper variety NUN 70064 PPH with a transgene that confers the desired trait, wherein the transformed plant contains the desired trait and otherwise has all of the physiological and morphological characteristics of the plant of pepper variety NUN 70064 PPH.

The disclosure also provides a method of producing a modified pepper plant with a desired trait, wherein the method comprises mutating a target gene by targeted gene editing in a pepper plant or plant part of pepper variety NUN 70064 PPH, wherein the target gene modifies a desired trait.

In one aspect, the single locus conversion or desired trait is yield, storage properties, color, flavor, size, firmness, enhanced nutritional quality, post-harvest quality, male sterility, herbicide tolerance, insect resistance, pest resistance, disease resistance, environmental stress tolerance, modified carbohydrate metabolism, modified protein metabolism, or ripening.

In another aspect, the disclosure provides a container comprising the plant, plant part, or seed of pepper variety NUN 70064 PPH.

Also provided is a food, a feed, or a processed product comprising a plant part of pepper variety NUN 70064 PPH, wherein the plant part is a fruit or a part thereof.

BRIEF DESCRIPTION OF THE DRAWINGS

FIG. 1 shows the immature fruit of pepper variety NUN 70064 PPH.

DEFINITIONS

"Pepper" refers herein to plants of the species *Capsicum annuum* or *frutescens*, and fruits thereof. The most commonly eaten part of a pepper is the fruit. The fruit comprises a stem or peduncle or pedicel, calyx, placenta, fruit wall, veins, shoulder, base, apex, locule or lobe, septa, exocarp, mesocarp, endocarp, pericarp, optionally secondary peppers, optionally capsaicin glands and optionally seed. The stem or peduncle or pedicel, calyx, placenta, fruit wall, veins, shoulder, base, apex, locule or lobe, septa, exocarp, mesocarp, endocarp, pericarp, secondary peppers, capsaicin glands and seed coat of the seed are maternal tissues, and thus they are genetically identical to the plant on which they grow.

"Cultivated pepper" refers to plants of *Capsicum annuum*, or a closely related species, e.g., varieties, breeding lines or cultivars of the species *C. annuum* as well as crossbreds thereof, or crossbreds with other *Capsicum* species, cultivated by humans and having good agronomic characteristics.

The terms "pepper plant designated NUN 70064 PPH," "NUN 70064 PPH," "NUN 70064," "NUN 70064 F1," "70064 PPH," or "pepper 70064," are used interchangeably herein and refer to a pepper plant of variety NUN 70064 PPH, representative seed of which has been deposited under Accession Number NCIMB 44718.

A "seed of NUN 70064 PPH" refers to a pepper seed which can be grown into a plant of variety NUN 70064 PPH, wherein a representative sample of viable seed of said pepper variety has been deposited under Accession Number NCIMB 44718. A seed can be in any stage of maturity, for example, a mature, viable seed, or an immature, non-viable seed. A seed comprises an embryo and maternal tissues.

An "embryo of NUN 70064 PPH" refers to an "F1 hybrid embryo" as present in a seed of pepper variety NUN 70064 PPH, a representative sample of said seed of said pepper variety has been deposited under Accession Number NCIMB 44718.

A "seed grown on NUN 70064 PPH" refers to a seed grown on a mature plant of variety NUN 70064 PPH or inside a fruit of pepper variety NUN 70064 PPH. The "seed grown on NUN 70064 PPH" contains tissues and DNA of the maternal parent, pepper variety NUN 70064 PPH. The "seed grown on NUN 70064 PPH" contains an F2 embryo. When said seed is planted, it grows into a first generation progeny plant of variety NUN 70064 PPH.

A "fruit of NUN 70064 PPH" refers to a fruit containing maternal tissues of pepper variety NUN 70064 PPH as deposited under Accession Number NCIMB 44718. In one aspect, the fruit does not contain seed, i.e., the fruit is parthenocarpic. The skilled person is familiar with methods for inducing parthenocarpy. Those methods comprise chemically or genetically inducing parthenocarpy. Compounds suitable for chemically inducing parthenocarpy include auxins, gibberellins and cytokinins. Genetic parthenocarpy can be induced by CaARF8 mutants (see, e.g., Tiwari et al., *BMC Plant Biology* 2011, 11:143 DOI: 10.1186/1471-2229-11-143 or U.S. Pat. No. 8,492,619, which are herein incorporated by reference in their entireties). A fruit can be in any stage of maturity, for example, comprising viable seed or comprising immature non-viable seed.

An "essentially homogeneous population of pepper seed" is a population of seeds where at least 97%, 98%, 99% or more of the total population of seed are seed of pepper variety NUN 70064 PPH.

An "essentially homogeneous population of pepper plants" is a population of plants where at least 97%, 98%, 99% or more of the total population of plants are plants of variety NUN 70064 PPH.

The phrase "essentially free from other seed" refers to a population of seed where less than 3%, 2%, 1% or less of the total population of seed is seed that is not a pepper seed or, in another option, less than 3%, 2%, 1% or less of the total population of seed is seed that is not seed of pepper variety NUN 70064 PPH.

"USDA descriptors" are the plant variety descriptors for pepper (*Capsicum* spp.) as published by the US Department of Agriculture, Agricultural Marketing Service, Plant Variety Protection Office, Beltsville, MD 20705, and which can be downloaded from the world wide web at ams.usda.gov under services/plant-variety-protection/pvpo-c-forms under pepper. "Non-USDA descriptors" are other descriptors suitable for describing pepper.

"UPOV descriptors" are the plant variety descriptors described for pepper in the "Guidelines for the Conduct of Tests for Distinctness, Uniformity and Stability, TG/76/8 (Geneva 2006, revised 2018), as published by UPOV (International Union for the Protection of New Varieties and Plants, and which can be downloaded from the world wide web at upov.int under edocs/tgdocs/en/tg076.pdf and is herein incorporated by reference in its entirety. Likewise, "UPOV methods" to determine specific parameters for the characterization of pepper are described at upov.int.

"Calibration book *Capsicum annuum* L." refers to the calibration book for pepper which provides guidance for describing a pepper variety, as published by Naktuinbow (December 2010, version 1) and based on the UPOV Guideline TG/76/8 and CPVO (Community Plant Variety Office) Protocol CPVO-TP/076/2.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007.

"Reference Variety for NUN 70064 PPH" refers herein to variety Mixteco, a commercial variety from HM Clause, which has been planted in a trial together with pepper variety NUN 70064 PPH.

"Plant" includes the whole plant or any part or derivatives thereof, preferably having the same genetic makeup as the plant from which it is obtained.

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, hypocotyl, cotyledon, a scion, a graft, a stock, a rootstock, a pistil, an anther, and a flower or part thereof. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises the maternal tissues of pepper variety NUN 70064 PPH and an embryo having one or two sets of chromosomes derived from the parent plant, e.g., from pepper variety NUN 70064 PPH. Such an embryo comprises two sets of chromosomes derived from pepper variety NUN 70064 PPH, if it is produced from self-pollination, while an embryo derived from cross-fertilization of pepper variety NUN 70064 PPH will comprise only set of chromosomes from said variety.

"Rootstock" or "stock" refers to the plant selected for its roots, in particular for the resistance of the roots to diseases or stress (e.g., heat, cold, salinity etc.). Normally, the quality of the fruit of the plant providing the rootstock is less important.

"Scion" refers to a part of the plant attached to the rootstock. This plant is selected for its stems, leaves, flowers, or fruits. The scion contains the desired genes to be duplicated in future production by the stock/scion plant and may produce the desired pepper fruit.

"Stock/scion" or grafted plant refers to a pepper plant comprising a rootstock from one plant grafted to a scion from another plant.

"Harvest maturity" is referred to as the stage at which a pepper fruit is ripe or ready for harvest or the optimal time to harvest the fruit for the market, for processing or for consumption. In one aspect, harvest maturity is the stage which allows proper completion of the normal ripening.

"Harvested plant material" refers herein to plant parts (e.g., fruits detached from the whole plant), which have been collected for further storage and/or further use.

"Yield" means the total weight of all pepper fruits harvested per hectare of a particular line or variety. It is understood that "yield" expressed as weight of all pepper fruits harvested per hectare can be obtained by multiplying the number of plants per hectare times the "yield per plant".

"Marketable yield" means the total weight of all marketable pepper fruits, especially fruit that is not cracked, damaged or diseased, harvested per hectare of a particular line or variety. A "marketable fruit" is a fruit that has commercial value.

"Flavor" refers to the sensory impression of a food or other substance, especially a pepper fruit or fruit part (fruit flesh) and is determined mainly by the chemical senses of taste and smell. Flavor is influenced by texture properties and by volatile and/or non-volatile chemical components (organic acids, lipids, carbohydrates, salts, etc.).

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two, or three of the physiological and morphological characteristics" of a referred-to-plant, or "all the physiological and morphological characteristics" of Table 1 "all or all but one, two, or three of the physiological and morphological characteristics" of Table 1.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted Plant or a mutated plant of pepper variety NUN 70064 PPH, may have one or more (or all) of the physiological and/or morphological characteristics of said variety listed in Table 1, as determined at the 5% significance level (i.e., $p<0.05$) when grown under the same environmental conditions.

"Distinguishing characteristics" or "distinguishing morphological and/or physiological characteristics" refers herein to the characteristics which distinguish (i.e., are different) between the new pepper variety from other pepper varieties, such as the Reference Variety when grown under the same environmental conditions. When comparing pepper variety NUN 70064 PPH with different varieties, the distinguishing characteristics may be different. In one aspect, the distinguishing characteristics may therefore include at least one, two, three or more (or all) of the characteristics listed in Table 1. All numerical distinguishing characteristics are statistically significantly different at $p<0.05$ between pepper variety NUN 70064 PPH and the other variety, e.g., the Reference Variety.

Thus, a pepper plant "comprising the distinguishing characteristics of pepper variety NUN 70064 PPH" (such as a progeny plant) refers herein to a plant which does not differ significantly from said variety in the distinguishing characteristics above, Therefore, in one aspect, a plant (such as a progeny plant of variety NUN 70064 PPH) is provided which does not differ significantly from pepper variety NUN 70064 PPH in the distinguishing characteristics above.

Similarity and differences between two different plant lines or varieties can be determined by comparing the number of morphological and/or physiological characteristics (e.g. the characteristics as listed in Table 1) that are the same (i.e., statistically not significantly different) or that are different (i.e., statistically significantly different) between the two plant lines or varieties when grown under the same environmental conditions. A numerical characteristic is considered to be "the same" when the value for a numeric characteristic is not significantly different at the 1% ($p<0.01$) or 5% ($p<0.05$) significance level, using T-test, a standard method known to the skilled person. Non-numerical or "degree" or "type" characteristic is considered "the same" when the values have the same "degree" or "type" when scored using USDA and/or UPOV descriptors, if the plants are grown under the same environmental conditions.

In one aspect, a statistical analysis of the quantitative characteristics showing the degree of significance may be provided. Statistical significance is the likelihood that a relationship between two or more variables is caused by something other than chance, i.e., that the differences in the means for quantitative characteristics of the plant of pepper variety NUN 70064 PPH and the Reference Variety are significant due to chance. For the purpose of proving differences or distinction between pepper variety NUN 70064 PPH and the Reference Variety, a p-value of 5% or 0.05 or lower is considered statistically significant. This means that there is only a 5% probability that the observed result could have happened just by chance or random variation.

The statistical analysis is drawn from a small sample of at least 15 plants or plant parts of pepper variety NUN 70064 PPH and the Reference Variety. Statistical points or parameters such as mean, minimum, median, maximum, and standard deviation are collected from the sample data to analyze where the average is, how varied the data set is, and whether the data is skewed. For the purpose of determining whether the result of the data set is statistically significant, a T-Test is used, a statistical tool for proving significance in the means of the two groups (e.g., pepper variety NUN 70064 PPH and the Reference Variety) at 5% significance level (a p-value of 5% or 0.05).

The term "traditional breeding techniques" encompasses herein crossing, selfing, selection, doubled haploid production, embryo rescue, protoplast fusion, marker assisted selection, mutation breeding, etc. as known to the breeder (e.g., methods other than genetic modification/transformation/transgenic methods), by which, for example, a genetically heritable trait can be transferred from one pepper line or variety to another.

"Variety" or "cultivar" means a plant grouping within a single botanical taxon of the lowest known rank.

A "plant line" is for example a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Tissue culture" or "cell culture" refers to a composition comprising isolated cells of the same or a different type or a collection of such cells organized into parts of a plant. Tissue culture of various tissues of pepper and regeneration of plants therefrom is well known and widely published (see, e.g., Sang-Gu et al. (1988), Plant Cell, Tissue and Organ Culture 12: 67-74; Kothari et al., (2010) Biotechnology Advances 28: 35-48). Similarly, the skilled person is well-aware how to prepare a "tissue culture" or "cell culture."

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 70064 PPH. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another pepper plant of the same variety or another variety or (breeding) line, or with wild pepper plants. A progeny may comprise a mutation or a transgene. A first generation progeny" or is the progeny directly derived from, obtained from, obtainable from or derivable from the parent plant by, e.g., traditional breeding methods (selfing and/or cross-pollinating) or regeneration (optionally combined with transformation and mutation). Thus, a plant of variety NUN 70064 PPH, is the male parent, the female parent or both of a first generation progeny of that variety or both of a first generation progeny of pepper variety NUN 70064 PPH. Progeny may have all the physiological and morphological characteristics of variety NUN 70064 PPH when grown under the same environmental conditions and/or progeny may have (be selected for having) one or more of the distinguishing characteristics of pepper of the disclosure. Using common breeding methods such as backcrossing or recurrent selection, mutation or transformation, one or more specific characteristics may be introduced into said variety, to provide or a plant comprising all but 1, 2, or 3 or more of the morphological and physiological characteristics of variety NUN 70064 PPH.

The terms "gene converted" or "conversion plant" or "single locus converted plant" in this context refer to pepper plants which are developed by traditional breeding techniques e.g., backcrossing or via genetic engineering or through mutation breeding, wherein essentially all of the desired morphological and physiological characteristics of the parent variety or line are recovered, in addition to the one or more genes transferred into the parent via e.g., backcrossing technique (optionally including reverse breeding or reverse synthesis of breeding lines). It is understood that only the addition of a further characteristic (e.g., addition of gene conferring a further characteristic, such as a disease resistance gene), but also the replacement/modification of an existing characteristic by a different characteristic is encompassed herein.

Likewise, a "Single Locus Converted (Conversion) Plant" refers to a plant developed by plant breeding techniques comprising or consisting of mutation and/or by genetic transformation and/or by traditional breeding techniques, such as backcrossing, wherein essentially all of the desired morphological and physiological characteristics of a pepper variety are recovered in addition to the characteristics of the single locus having been transferred into the variety via the backcrossing technique. In case of a hybrid, the gene may be introduced in the male or female parental line.

"Transgene" or "chimeric" gene" refers to a genetic locus comprising a DNA sequence which has been introduced into the genome of the plant by transformation. A plant comprising a transgene stably integrated into its genome is referred to as "transgenic plant."

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

"Average" refers herein to the arithmetic mean.

The term "mean" refers to the arithmetic mean of several measurements. The skilled person understands that the appearance of a plant depends to some extent on the growing conditions of said plant. The mean, if not indicated otherwise within this application, refers to the arithmetic mean of measurements on at least 15 different, randomly selected plants of a variety or line.

DETAILED DESCRIPTION OF VARIOUS ASPECTS OF THE DISCLOSURE

The disclosure relates to a plant of variety NUN 70064 PPH, wherein a representative sample of seeds of said variety has been deposited under the Budapest Treaty, with Accession Number NCIMB 44718. NUN 70064 PPH is a jalapeño pepper variety for the fresh market and is suitable for growing in the open field.

The disclosure also provides a pepper plant, or part thereof, having all of the physiological and morphological characteristics of pepper variety NUN 70064 PPH when grown under the same environmental conditions.

In another aspect, pepper variety NUN 70064 PPH or a progeny thereof comprises resistance to Tomato Spotted Wilt Virus (TSWV), measured according to UPOV standards described in TG/76/8.

The disclosure also provides a plant of variety NUN 70064 PPH, or a part thereof, or a progeny plant thereof, comprising all of the following morphological and/or physiological characteristics (i.e., average values, as indicated on the USDA Objective description of variety—pepper (unless indicated otherwise)) as shown in Table 1, determined at 5% significance level for numerical characteristics and determined by type or degree for plants for non-numerical characteristics when grown under the same environmental conditions. A part of this plant is also provided.

The disclosure further provides a pepper plant which does not differ from the physiological and morphological characteristics of the plant of variety NUN 70064 PPH as determined at the 1%, 2%, 3%, 4% or 5% significance level when grown under the same environmental conditions. In a particular aspect, the plants are measured in the same trial (e.g., the trial is conducted as recommended by the USDA or UPOV). The disclosure also comprises a part of said plant, preferably a fruit or part thereof.

The morphological and/or physiological differences between two different individual plants of the disclosure (e.g., between pepper variety NUN 70064 PPH, and a progeny thereof) or between a plant of variety NUN 70064 PPH or progeny of said variety, or a plant having all, or all but 1, 2, or 3, of the physiological and morphological characteristics of variety NUN 70064 PPH (or all, or all but 1, 2, or 3 of the characteristics as listed in Table 1) and another known variety can easily be established by growing said variety next to each other or next to the other variety (in the same field, under the same environmental conditions), preferably in several locations which are suitable for said pepper cultivation, and measuring morphological and/or physiological characteristics of a number of plants (e.g., to calculate an average value and to determine the variation range/uniformity within the variety). For example, trials can be carried out in Acampo CA, USA (N 38 degrees 07'261"/W 121 degrees 18' 807", USA), whereby various characteristics, for example, maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of pepper.

Thus, the disclosure comprises pepper plant having one, two, or three physiological and/or morphological characteristics which are different from those of the plant of variety NUN 70064 PPH and which otherwise has all the physiological and morphological characteristics of said variety, when determined at the 5% significance level for numerical characteristics and determined by type or degree for non-numerical characteristics for plants grown under the same environmental conditions. In a particular aspect, the different characteristic(s) is/are result of breeding with pepper variety NUN 70064 PPH and selection of progeny plant comprising 1, 2, or 3 characteristics which are different than in pepper variety NUN 70064 PPH. In another aspect, the different characteristic is the result of a mutation (e.g., spontaneous mutation or a human induced mutation through e.g., targeted mutagenesis or traditional mutagenesis such as chemically or radiation induced mutagenesis), or it is the result of transformation.

The disclosure also relates to a seed of pepper variety NUN 70064 PPH, wherein a representative sample of said seed has been deposited under the Budapest Treaty with Accession Number NCIMB 44718.

In another aspect, a seed of hybrid variety NUN 70064 PPH is obtainable by crossing the male parent of pepper variety NUN 70064 PPH with the female parent pepper variety NUN 70064 PPH and harvesting the seeds produced on the female parent. The resultant seeds of said variety can be grown to produce plants of said variety.

In another aspect, the disclosure provides a plant grown from a seed of pepper variety NUN 70064 PPH and plant part thereof.

The disclosure also provides a pepper fruit produced on a plant grown from a seed of pepper variety NUN 70064 PPH.

In another aspect, the disclosure provides for a pepper plant part of variety NUN 70064 PPH, preferably a fruit, a representative sample of seed from said variety has been deposited under the Budapest Treaty with Accession Number NCIMB 44718.

Also provided is a plant of pepper variety NUN 70064 PPH, or a fruit or other plant part thereof, produced from a seed, wherein a representative sample of said seeds has been deposited under the Budapest Treaty with Accession Number NCIMB 44718.

Also a plant part obtained from variety NUN 70064 PPH, is provided, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, a hypocotyl, a cotyledon, a scion, a stock, a rootstock, a pistil, an anther, and a flower or a part thereof. Fruits are particularly important plant parts. Fruits may be parthenocarpic, or seedless, or contain immature and/or nonviable seeds.

In a further aspect, the plant part obtained from variety NUN 70064 PPH is a cell, optionally a cell in a cell or tissue culture. That cell may be grown into a plant of variety NUN 70064 PPH. A part of a variety of NUN 70064 PPH (or of progeny variety NUN 70064 PPH, or of a plant having all physiological and/or morphological characteristics but one, two, or three which are different from those of variety NUN 70064 PPH) further encompasses any cells, tissues, organs obtainable from the seedlings or plants in any stage of maturity.

The disclosure also provides a tissue or cell culture comprising cells of pepper variety NUN 70064 PPH. Such a tissue culture can, for example, be grown on plates or in liquid culture, or be frozen for long term storage. The cells of pepper variety NUN 70064 PPH, used to start the culture can be selected from any plant part suitable for vegetative reproduction, or in a particular aspect can be one or more of an embryo, meristem, a cotyledon, a hypocotyl, pollen, a leaf, an anther, a root, a root tip, a pistil, a petiole, a flower, a fruit, seed, and/or a stem. In another particular aspect, the tissue culture does not contain somaclonal variation or has reduced somaclonal variation. The skilled person is familiar with methods to reduce or prevent somaclonal variation, including regular reinitiation.

In one aspect, the disclosure provides a pepper plant regenerated from the tissue or cell culture of pepper variety NUN 70064 PPH, wherein the regenerated plant is not significantly different from pepper variety NUN 70064 PPH in all, or all but one, two, or three, of the physiological and morphological characteristics, e.g. determined at the 5% significance level for numerical characteristics and determined by type or degree for non-numerical characteristics when grown under the same environmental conditions. Optionally, the plant has one, two, or three the physiological and morphological characteristics that are affected by a mutation or by transformation. In another aspect, the disclosure provides a pepper plant regenerated from the tissue or cell culture of pepper variety NUN 70064 PPH, wherein the plant has all of the physiological and morphological characteristics of said variety, e.g., determined at the 5% significance level for numerical characteristics and determined by type or degree for non-numerical characteristics when grown under the same environmental conditions. Similarity or difference of a characteristic is determined by measuring the characteristics of a representative number of plants grown under the same environmental conditions, determining whether type/degree characteristics are the same and determining whether numerical characteristics are different at the 5% significance level.

Pepper variety NUN 70064 PPH, or its progeny, or a plant having all physiological and/or morphological characteristics but one, two, or three which are different from those of pepper variety NUN 70064 PPH can also be reproduced using vegetative reproduction methods. Therefore, the disclosure provides for a method of producing a plant, or a part thereof, of variety NUN 70064 PPH, comprising vegetative propagation of said variety. Vegetative propagation comprises regenerating a whole plant from a plant part of variety NUN 70064 PPH, (or from a progeny of said variety or from or a plant having all physiological and/or morphological characteristics of said variety but one, two, or three different characteristics), such as a cutting, a cell culture or a tissue culture.

The disclosure also concerns methods of vegetatively propagating a part of the plant of pepper variety NUN 70064 PPH. In certain aspects, the method comprises: (a) collecting tissue or cells capable of being propagated from a plant described herein; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one aspect, the method further comprises step (d) growing plants from said rooted plantlets. Therefore, the method also comprises regenerating a whole plant from said part of NUN 70064 PPH. In a particular aspect, the part of the plant to be propagated is a cutting, a cell culture or a tissue culture.

The disclosure also provides for a vegetatively propagated plant of variety NUN 70064 PPH (or from progeny of said variety or from or a plant having all but one, two or three physiological and/or morphological characteristics of said variety), wherein the plant has all of the morphological and physiological characteristics of variety NUN 70064 PPH, e.g., determined at the 5% significance level for numerical characteristics and determined by type or degree for plants grown under the same environmental conditions. In another aspect, the propagated plant has all but one, two, or three of the morphological and physiological characteristics of variety NUN 70064 PPH, e.g., determined at the 5% significance level for numerical characteristics and determined by type or degree for non-numerical characteristics for plants grown under the same environmental conditions. A part of said propagated plant or said propagated plant with one, two or three differences is also included. In another aspect, the propagated plant has all or all but, 1, 2, or 3 of the physiological and morphological characteristics of pepper variety NUN 70064 PPH (e.g., as listed in Table 1).

In another aspect, the disclosure provides a method for producing a pepper plant part, preferably a fruit, comprising growing a plant of variety NUN 70064 PPH until it sets at least one fruit, and collecting the fruit. Preferably, the fruit is collected at harvest maturity. In another aspect, the fruit is collected when the seed is ripe.

In another aspect, a plant of variety NUN 70064 PPH can be produced by seeding directly in the soil (e.g., field) or by germinating the seeds in controlled environment conditions (e.g., greenhouses) and optionally then transplanting the seedlings into the field. For example, the seed can be sown into prepared seed beds where they will remain for the entire production the crop (see, Hartz, et. al, University of California Division of Agriculture and Natural Resources, Publication 7217, 1-4). Stakes and plastic mulches may also be used for peppers for the fresh the market, particularly, when peppers are to be harvested at mature fruit color and to promote earliness and yield. On the other hand, no stake or mulch is used for processing peppers. Moreover, pepper can also be grown entirely in greenhouses or tunnels.

In another aspect, the disclosure provides a progeny plant of variety NUN 70064 PPH, such as a progeny plant obtained by further breeding that variety. Further breeding with the variety includes selfing that variety one or more times and/or cross-pollinating that variety with another pepper plant or variety one or more times. In particular, the disclosure provides for a progeny plant that retains all the morphological and physiological characteristics of pepper variety NUN 70064 PPH, or, in another aspect, a progeny plant that retains all, or all but one, two, or three, of the morphological and physiological characteristics of variety NUN 70064 PPH, optionally all or all but one, two, or three of the characteristics as listed in Table 1, e.g., determined at the 5% significance level for numerical characteristics and determined by type or degree for non-numerical characteristics when grown under the same environmental conditions. In a particular aspect, the progeny is a first generation progeny, i.e., the ovule or the pollen (or both) used in the crossing is an ovule or pollen of variety NUN 70064 PPH, where the pollen comes from an anther of and the ovule comes from an ovary of variety NUN 70064 PPH and the ovule comes from an ovary of pepper variety NUN 70064 PPH.

In still another aspect, the disclosure provides a method of producing a pepper plant, comprising crossing a plant of pepper variety NUN 70064 PPH with a second pepper plant at least once, allowing seed to develop and optionally harvesting said progeny seed. The skilled person can select progeny from said crossing. Optionally, the progeny (grown from the progeny seed) is crossed twice, thrice, or four, five, six or seven times, and allowed to set seed. In one aspect of the disclosure, the first "crossing" further comprises planting seeds of a first and a second parent pepper plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

The disclosure also provides a method for collecting pollen, comprising collecting pollen from a pepper variety NUN 70064 PPH. Alternatively, the method comprises growing a plant of variety NUN 70064 PPH until at least one flower contains pollen and collecting the pollen. In particular aspect, the pollen is collected when it is mature or ripe. A suitable method for collecting pollen comprises collecting anthers or the part of the anther that contains pollen, for example by cutting the anther or the part of the anther off. Pollen can be collected in a container. Optionally, collected pollen can be used to pollinate a pepper flower.

In yet another aspect, the disclosure provides a method of producing a plant, comprising selfing a plant of variety NUN 70064 PPH one or more times, and selecting a progeny plant from said selfing. In one aspect, the progeny plant retains all or all but one, two, or three of the morphological and physiological characteristics of variety NUN 70064 PPH when grown under the same environmental conditions. In a different aspect, the progeny plant comprises all (or all but one, two, or three) of the physiological and morphological characteristic of variety NUN 70064 PPH of Table 1.

The disclosure also provides a method for developing a pepper plant in a pepper breeding program, using a pepper plant described herein, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing pepper variety NUN 70064 PPH, or progeny of said variety, or a plant comprising all but 1, 2, or 3 or more of the morphological and physiological characteristics of variety NUN 70064 PPH (e.g., as listed in Table 1), with a different pepper plant, and wherein one or more offspring of the crossing are subject to one or more plant breeding techniques: recurrent selection, backcrossing, pedigree breeding, mass selection, mutation breeding and genetic marker enhanced selection (see e.g., Martin et al. 2008, Australian Journal of Crop Science 1(2): 43-46). For breeding methods in general (see, e.g., Principles of Plant Genetics and Breeding, 2007, George Acquaah, Blackwell Publishing, ISBN-13: 978-1-4051-3646-4).

In one aspect, pedigree selection is used as a breeding method for developing a pepper variety. Pedigree selection is also known as the "Vilmorin System of Selection," see, e.g., Allard, John Wiley & Sons, Inc., 1999, pp. 64-67. In general, selection is first practiced among F2 plants. In the next season, the most desirable F3 lines are first identified, then desirable F3 plants within each line are selected. The following season and in all subsequent generations of inbreeding, the most desirable families are identified first, then desirable lines within the selected families are chosen. A family refers to lines that were derived from plants selected from the same progeny from the preceding generation.

Thus, progeny in connection with pedigree selection are either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g., F2) with another pepper plant (and/or with a wild relative of pepper). Progeny may have all the physiological and morphological characteristics of pepper variety NUN 70064 PPH when grown under the same environmental conditions and/or progeny may have (be selected for having) one or more of the distinguishing characteristics of pepper variety NUN 70064 PPH.

In yet a further aspect, the disclosure provides for a method of producing a pepper plant. The method comprises crossing a plant of variety NUN 70064 PPH, or a plant comprising all but 1, 2, or 3 of the morphological and physiological characteristics of pepper variety NUN 70064 PPH (e.g., as listed in Table 1), or a progeny plant thereof, either as male or as female parent, with a second pepper plant (or a wild relative of pepper) one or more times, and/or selfing a pepper plant of variety NUN 70064 PPH, or a progeny plant thereof, one or more times, and selecting progeny from said crossing and/or selfing. The second pepper plant may, for example, be a line or variety of the species *Capsicum annuum, C. frutecens, C. baccatum, C. chinense*, or other *Capsicum* species.

In a further aspect, pepper variety NUN 70064 PPH is used in crosses with other, different, pepper varieties to produce first generation (F1) pepper hybrid seeds and plants with superior characteristics. In a particular aspect, the disclosure provides a pepper seed and a plant produced by crossing a first parent pepper plant with a second parent pepper plant, wherein at least one of the first or second parent pepper plant is pepper variety NUN 70064 PPH. In another aspect, the pepper seed and plant produced are the first filial generation (F1) pepper seed and plants produced by crossing the plant of pepper variety NUN 70064 PPH with another pepper plant.

The morphological and physiological characteristics (and the distinguishing characteristics) of pepper variety NUN 70064 PPH are provided, e.g., Table 1. Encompassed herein is also a plant obtainable from pepper variety NUN 70064 PPH (e.g., by selfing and/or crossing and/or backcrossing with said variety and/or progeny of said variety) comprising all or all but one, two, or three of the physiological and morphological characteristics of variety NUN 70064 PPH e.g., as listed in Table 1 when determined at the 5% significance level for numerical characteristics or determined by type or degree for non-numerical characteristics when grown under the same environmental conditions and/or comprising one or more (or all; or all except one, two, or three) characteristics when grown under the same environmental conditions. The morphological and/or physiological characteristics may vary somewhat with variation in the environment (such as temperature, light intensity, day length, humidity, soil, fertilizer use), which is why a comparison under the same environmental conditions is preferred. Colors can best be measured using the Royal Horticultural Society Chart.

In another aspect, the disclosure provides a method of producing a plant derived from pepper variety NUN 70064 PPH, comprising crossing a plant of pepper variety NUN 70064 PPH either as a male or female parent with a second plant or selfing pepper variety NUN 70064 PPH or vegetative reproduction of pepper variety NUN 70064 PPH and collecting seeds from said crossing or selfing or regenerating a whole plant from the vegetable cell- or tissue culture. Also provided are seeds and/or plants obtained by this method. All plants produced using pepper variety NUN 70064 PPH as a parent are within the scope of the disclosure, including plant parts derived from pepper variety NUN 70064 PPH.

In further aspects, the method comprises growing a progeny plant of a subsequent generation and crossing the progeny plant of a subsequent generation with itself or a second plant and repeating the steps for additional 3-10 generations to produce a plant derived from pepper variety NUN 70064 PPH. The plant derived from pepper variety NUN 70064 PPH may be an inbred line and the aforementioned repeating crossing steps may be defined as comprising sufficient inbreeding to produce the inbred line. By selecting plants having one or more desirable traits of the line as well as potentially other selected traits.

The disclosure provides for methods of producing plants which retain all the morphological and physiological characteristics of a plant of variety NUN 70064 PPH. The disclosure provides also for methods of producing a plant comprising all but 1, 2, or 3 or more of the morphological and physiological characteristics of variety NUN 70064 PPH (e.g., as listed in Table 1), but which are still genetically closely related to said variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to variety NUN 70064 PPH, if its DNA fingerprint is at least 80%, 90%, 95% or 98% identical to the fingerprint of said variety. In a particular aspect, AFLP markers are used for DNA fingerprinting (see, e.g., Vos et al. 1995, Nucleic Acid Research 23: 4407-4414). A closely related plant may have a Jaccard's Similarity index of at least about 0.8, preferably at least about 0.9, 0.95, 0.98 or more (see, e.g., Ince, et. al., 2010, Biochem Genet 48:83-95). The disclosure also provides a plant and a variety obtained or selected by applying these methods on pepper variety NUN 70064 PPH. Such a plant may be produced by crossing and/or selfing, or alternatively, a plant may simply be identified and selected amongst plants of said variety, or progeny of said variety, e.g., by identifying a variant within pepper variety NUN 70064 PPH, or within progeny of said variety (e.g., produced by selfing) which variant differs from said variety in one, two, or three of the morphological and/or physiological characteristics (e.g., in one, two, or three distinguishing characteristics), e.g., as listed in Table 1. In one aspect, the disclosure provides a pepper plant having a Jaccard's Similarity index with pepper variety NUN 70064 PPH of at least 0.8, e.g., at least 0.85, 0.9, 0.95, 0.98 or even at least 0.99.

In another aspect, the disclosure provides a pepper plant comprising genomic DNA having at least 95%, 96%, 97%, 98% or 99% sequence identity compared to the genomic DNA sequence of a plant of variety NUN 70064 PPH as deposited under Accession Number NCIMB 44718. In some aspects, the pepper plant further comprises all or all but 1, 2, or 3 of the morphological and physiological characteristics of variety NUN 70064 PPH (e.g., as listed in Table 1). In other aspects, the pepper plant is a hybrid derived from a seed or plant of variety NUN 70064 PPH.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (see, e.g., EMBOSS, Rice et al., Trends in Genetics June 2000, vol. 16, No. 6. pp. 276-277).

In another aspect, a plant of variety NUN 70064 PPH may also be mutated (by e.g., irradiation, chemical mutagenesis, heat treatment, etc.) and mutated seeds or plants may be selected in order to change one or more characteristics of said variety. Methods such as TILLING (Targeting Induced Local Lesions in Genomes) may be applied to pepper populations in order to identify mutants.

Similarly, pepper variety NUN 70064 PPH may be transformed and regenerated, whereby one or more chimeric genes are introduced into the variety or into a plant comprising all but 1, 2, 3, or more of the morphological and physiological characteristics (e.g., as listed in Table 1). Many useful traits can be introduced into pepper variety NUN 70064 PPH by e.g., crossing pepper variety NUN 70064 PPH with a transgenic pepper plant comprising a desired transgene as well as by directly introducing a transgene into pepper variety NUN 70064 PPH by genetic transformation techniques.

Transformation can be carried out using standard methods, such as *Agrobacterium tumefaciens* mediated transformation or biolistics, followed by selection of the transformed cells and regeneration into plants. A desired trait (e.g., gene(s) conferring pest or disease resistance, herbicide, fungicide or insecticide tolerance, etc.) can be introduced into pepper variety NUN 70064 PPH, or progeny of said variety, by transforming said variety or progeny of said variety with a transgene that confers the desired trait, wherein the transformed plant retains all or all but one, two or three of the phenotypic and/or morphological and/or physiological characteristics of variety NUN 70064 PPH, or the progeny of said variety and contains the desired trait.

Any pest or disease resistance genes may be introduced into a plant of variety NUN 70064 PPH, progeny of said variety or into a plant comprising all but 1, 2, or 3 or more of the morphological and physiological characteristics of variety NUN 70064 PPH (e.g., as listed in Table 1). Resistance to one or more of the following diseases or pests may be introduced into plants of the disclosure: Cucumber Mosaic Virus, Curly Top Virus, Pepper Mild Mottle Virus, Potato Y Virus, Tobacco Etch Virus, Tobacco Mosaic Virus, Tomato Spotted Wilt Virus, Anthracnose (*Gloeosporium piperatum*), Bacterial Spot (*Xanthomonas vesicatoria*), Cercospora Leaf Spot (*Cercospora capsici*), Nematode (*Meloidogyne incognita acrita*), Phytophthora Root Rot (*Phytophthora capsici*), Ripe Rot (*Vermicularia capsici*), Southern Blight (*Sclerotium rolfsii*) and/or Verticillium Wilt (*Verticil-*

*lium dahliae*). Other resistance genes, against pathogenic viruses, fungi, bacteria, nematodes, insects or other pests may also be introduced.

Genetic transformation may, therefore, be used to insert a selected transgene into the pepper plants of the disclosure described herein or may, alternatively, be used for the preparation of transgenic pepper plants which can be used as a source of the transgene(s), which can be introduced into pepper variety NUN 70064 PPH by e.g., backcrossing. A genetic trait which has been engineered into the genome of a particular pepper plant may then be moved into the genome of another pepper plant (e.g., another variety) using traditional breeding techniques which are well known in the art. For example, backcrossing is commonly used to move a transgene from a transformed pepper variety into an already developed pepper variety and the resulting backcross conversion plant will then comprise the transgene(s).

Any DNA sequences, whether from a different species or from the same species, which are inserted into the genome using transformation, are referred to herein collectively as "transgenes." A "transgene" also encompasses antisense, or sense and antisense sequences capable of gene silencing. Thus, the disclosure also relates to transgenic plants of pepper variety NUN 70064 PPH. In some aspects, a transgenic plant of pepper variety NUN 70064 PPH may contain at least one transgene but could also contain at least 1, 2, 3, 4, or more transgenes.

Plant transformation involves the construction of an expression vector which will function in plant cells. Such a vector comprises DNA comprising a gene under control of, or operatively linked to a regulatory element active in plant cells (e.g., promoter). The expression vector may contain one or more such operably linked gene/regulatory element combinations. The vector may be in the form of a plasmid and can be used alone or in combination with other plasmids to provide transformed pepper plants using transformation methods to incorporate transgenes into the genetic material of the pepper plant(s). Transformation can be carried out using standard methods, such as *Agrobacterium tumefaciens* mediated transformation, electroporation, biolistics particle delivery system, or microprojectile bombardment, followed by selection of the transformed cells and regeneration into plants.

Plants can also be genetically engineered, modified, or manipulated to express various phenotypes of horticultural interest. Through the transformation of pepper, the expression of genes can be altered to enhance disease resistance, insect resistance, herbicide resistance, stress tolerance, horticultural quality, and other traits. Transformation can also be used to insert DNA sequences which control or help control male sterility or fertility restoration. DNA sequences native to pepper as well as non-native DNA sequences can be transformed into pepper and used to alter levels of native or non-native proteins. Various promoters, targeting sequences, enhancing sequences, and other DNA sequences can be inserted into the genome for the purpose of altering the expression of proteins. Reduction of the specific activity of specific genes (also known as gene silencing or gene suppression) is desirable for several aspects of genetic engineering in plants.

Genome editing is another method recently developed to genetically engineer plants. Specific modification of chromosomal loci or targeted mutation can be done through sequence-specific nucleases (SSNs) by introducing a targeted DNA double strand break in the locus to be altered. Examples of SSNs that have been applied to plants are: finger nucleases (ZFNs), transcription activator-like effector nucleases (TALENs), engineered homing endonucleases or meganucleases, and clustered regularly interspaced short palindromic repeats (CRISPR)/CRISPR-associated protein 9 (Cas9), see, e.g., Songstad, et. al., Critical Reviews in Plant Sciences, 2017, 36:1, 1-23.

Thus, the disclosure also provides a method of producing a pepper plant comprising a desired trait, said method comprising mutating a plant, or plant part, of pepper variety NUN 70064 PPH and selecting a pepper plant comprising the desired trait, wherein the mutated plant contains the desired trait and otherwise retains all of the physiological and morphological characteristics of pepper variety NUN 70064 PPH, optionally as described in Table 1, wherein a representative sample of seed of said variety is deposited under Accession Number NCIMB 44718. In a further aspect, the desired trait is yield, compact pepper, fruit quality, male sterility, herbicide tolerance, insect resistance, pest resistance, disease resistance, Powdery mildew resistance without necrosis, environmental stress tolerance, modified carbohydrate metabolism, modified protein metabolism, or ripening.

In one aspect, the disclosure provides a method for inducing mutation in pepper variety NUN 70064 PPH, comprising:
a. exposing the seed, plant or plant part or cell of variety NUN 70064 PPH to a mutagenic compound or to radiation, wherein a representative sample of seed of said pepper variety is deposited under Accession Number NCIMB 44718;
b. selecting the seed, plant or plant part or cell of variety NUN 70064 PPH, having a mutation; and
c. optionally growing and/or multiplying the seed, plant or plant part or cell of variety NUN 70064 PPH, having the mutation.

The disclosure also provides a method of producing a pepper plant having a desired trait, wherein the method comprises transforming the pepper plant with a transgene that confers the desired trait, wherein the transformed plant contains the desired trait and otherwise retains all of the physiological and morphological characteristics of the plant of variety NUN 70064 PPH. Thus, a transgenic pepper plant is provided which is produced by the method described above, wherein the plant otherwise has all of the physiological and morphological characteristics of the plant of variety NUN 70064 PPH and the desired trait.

In another aspect, the disclosure provides a method of producing a progeny of plant of variety NUN 70064 PPH, further comprising a desired trait, said method comprising transforming the plant of pepper variety NUN 70064 PPH with at least one transgene that confers the desired trait and/or crossing the plant of pepper variety NUN 70064 PPH with a transgenic pepper plant comprising a desired transgene so that the genetic material of the progeny that resulted from the cross contains the desired transgene(s). Also encompassed is the progeny produced by this method.

A desired trait (e.g., gene(s) conferring pest or disease resistance, or tolerance for protection, etc.) can be introduced into pepper variety NUN 70064 PPH, or progeny of said variety, by transforming said variety or progeny of said variety with a transgene that confers the desired trait, wherein the transformed plant retains all or all but one, two, or three of the morphological and/or physiological characteristics of pepper variety NUN 70064 PPH, or the progeny of said variety, and contains the desired trait. In another aspect, the transformation or mutation confers a trait wherein the trait is yield, compact pepper, fruit quality, male sterility, herbicide tolerance, insect resistance, pest resistance, disease resistance, Powdery mildew resistance without necrosis, environmental stress tolerance, modified carbohydrate metabolism, modified protein metabolism, or ripening. In a particular aspect, the specific transgene may be any known in the art or listed herein, including, a polynucleotide sequence conferring resistance to imidazolinone, sulfonylurea, glyphosate, glufosinate, triazine, benzonitrile, cyclohexanedione, phenoxy proprionic acid and L-phosphinothricin or a polynucleotide conferring resistance to Cucumber Mosaic Virus, Curly Top Virus, Pepper Mild Mottle Virus, Potato Y Virus, Tobacco Etch Virus, Tobacco Mosaic Virus, Tomato Spotted Wilt Virus, Anthracnose (*Gloeosporium piperatum*), Bacterial Spot (*Xanthomonas vesicatoria*), Cercospora Leaf Spot (*Cercospora capsici*), Nematode (*Meloidogyne incognita acrita*), Phytophthora Root Rot (*Phytophthora capsici*), Ripe Rot (*Vermicularia capsici*), Southern Blight (*Sclerotium rolfsii*) and/or Verticillium Wilt (*Verticillium dahliae*). Other resistance genes, against pathogenic viruses, fungi, bacteria, nematodes, insects or other pests may also be introduced.

By crossing and/or selfing (one or more) single traits may be introduced into the plant of variety NUN 70064 PPH (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into the plant of pepper variety NUN 70064 PPH by breeding with said variety.

In another method, the step of introducing a single locus conversion in at least one of the parents comprises genetically transforming or mutating cells the parental line of pepper variety NUN 70064 PPH; growing the cells into a plant; and optionally selecting plants that contain the single locus conversion, the single trait conversion or the desired trait.

In another aspect, the step of introducing a single locus conversion, single trait conversion, or a desired trait in at least one of the parent lines comprises:

a. crossing the parental line of pepper variety NUN 70064 PPH, with a second pepper plant comprising the single locus conversion, the single trait conversion or the desired trait;

b. selecting F1 progeny plants that contain the single locus conversion, the single trait conversion or the desired trait;

c. crossing said selected progeny plants of step b) with the parental line of step a), to produce a backcross progeny plant;

d. selecting backcross progeny plants comprising the single locus conversion, the single trait conversion or the desired trait and otherwise all or all but one, two, or three of the morphological and physiological characteristics the parental line of step a) to produce selected backcross progeny plants; and e. optionally repeating steps c) and d) one or more times in succession to produce selected second, third or fourth or higher backcross progeny plants comprising the single locus conversion, the single trait conversion or the desired trait and otherwise all or all but one, two, or three of the morphological and physiological characteristics the parental line of step a) to produce selected backcross progeny plants when grown in the same environmental conditions.

The disclosure further relates to plants obtained by this method.

Alternatively, a single trait converted plant or single locus converted plant may be produced by:

a. obtaining a cell or tissue culture of cells of pepper variety NUN 70064 PPH;

b. genetically transforming or mutating said cells;

c. growing the cells into a plant; and d. optionally selecting plants that contain the single locus conversion, the single trait conversion, or the desired trait.

In another aspect, the disclosure provides a method of introducing a single locus conversion or single trait conversion, or a desired trait into pepper variety NUN 70064 PPH, comprising:

a. obtaining a combination of a parental lines of pepper variety NUN 70064 PPH, optionally through reverse synthesis of breeding lines;

b. introducing a single locus conversion in at least one of the parents of step a; and c. crossing the converted parent with the other parent of step a to obtain seed of pepper variety NUN 70064 PPH.

In another aspect, the disclosure provides a method of introducing a single locus conversion, or single trait conversion or a desired trait into pepper variety NUN 70064 PPH, comprising introducing a single locus conversion, or single trait conversion, or a desired trait in at least one of the parents of pepper variety NUN 70064 PPH; and crossing the converted parent with the other parent of pepper variety NUN 70064 PPH to obtain seed of pepper variety NUN 70064 PPH.

In the above methods, wherein the single locus conversion concerns a trait, the trait may be yield or pest resistance or disease resistance. In one aspect, the trait is disease resistance and the resistance is conferred to Cucumber Mosaic Virus, Curly Top Virus, Pepper Mild Mottle Virus, Potato Y Virus, Tobacco Etch Virus, Tobacco Mosaic Virus, Tomato Spotted Wilt Virus, Anthracnose (*Gloeosporium piperatum*), Bacterial Spot (*Xanthomonas vesicatoria*), Cercospora Leaf Spot (*Cercospora capsici*), Nematode (*Meloidogyne incognita acrita*), Phytophthora Root Rot (*Phytophthora capsici*), Ripe Rot (*Vermicularia capsici*), Southern Blight (*Sclerotium rolfsii*) and/or Verticillium Wilt (*Verticillium dahliae*). Other resistance genes, against pathogenic viruses, fungi, bacteria, nematodes, insects or other pests may also be introduced.

The disclosure also provides a plant having one, two, or three physiological and/or morphological characteristics which are different from those of pepper variety NUN 70064 PPH and which otherwise has all the physiological and morphological characteristics of said variety, wherein a representative sample of seed of said pepper variety is deposited under Accession Number NCIMB 44718. In particular, variants which differ from pepper variety NUN 70064 PPH, in none, one, two, or three of the characteristics mentioned in Table 1 are encompassed.

The disclosure also provides a pepper plant comprising at least a first set of the chromosomes of pepper variety NUN 70064 PPH, a sample of seed of said variety is deposited under Accession Number NCIMB 44718; optionally further comprising a single locus conversion or a mutation, wherein said plant has all of the morphological and physiological characteristics of the plant comprising at least a first set of the chromosomes of said variety. In another aspect, this single locus conversion confers a trait: yield, compact pepper, fruit quality, storage properties, color, male sterility, herbicide tolerance, insect resistance, pest resistance, disease resistance, environmental stress tolerance, modified carbohydrate metabolism, modified protein metabolism, or ripening.

In another aspect, the disclosure provides for a haploid plant and/or a doubled haploid plant of variety NUN 70064 PPH, or of a plant having all but one, two, or three physiological and/or morphological characteristics of variety NUN 70064 PPH, or progeny of said variety. Haploid and doubled haploid (DH) plants can, for example, be produced by cell or tissue culture and chromosome doubling agents and regeneration into a whole plant. DH production chromosome doubling may be induced using known methods, such as colchicine treatment or the like). In one aspect, the method comprises inducing a cell or tissue culture with a chromosome doubling agent and regenerating the cells or tissues into a whole plant.

In another aspect, the disclosure comprises a method for making doubled haploid cells from haploid cells of variety NUN 70064 PPH, said method comprising doubling cells of with a doubling agent, such as a colchicine treatment (see, e.g., Nikolova V, Niemirowicz-Szczytt K (1996) Acta Soc Bot Pol 65:311-317).

In yet another aspect, the disclosure provides for haploid plants and/or doubled haploid plants derived from pepper variety NUN 70064 PPH that, when combined, make a set of parents of pepper variety NUN 70064 PPH. The haploid plant and/or the doubled haploid plant of NUN 70064 PPH can be used in a method for generating parental lines of pepper variety NUN 70064 PPH.

The disclosure also provides methods for determining the identity of parental lines of plants described herein, in particular the identity of the female line. US2015/0126380, which is hereby incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of a plant of variety NUN 70064 PPH, is a progeny of said variety, because the seed coat of the seed is a maternal tissue genetically identical to said variety. In one aspect, the disclosure relates to a seed coat comprising maternal tissue of pepper variety NUN 70064 PPH. In another aspect, the disclosure relates to a pepper seed comprising a maternal tissue of pepper variety NUN 70064 PPH. In another particular aspect, the disclosure provides for a method of identifying the female parental line of pepper variety NUN 70064 PPH by analyzing the seed coat of a seed of that variety. In another aspect, the skilled person can determine whether a seed is grown on pepper variety NUN 70064 PPH by analyzing the seed coat of said seed.

Using methods known in the art such as "reverse synthesis of breeding lines" or "reverse breeding", it is possible to produce parental lines for a hybrid plant such as pepper variety NUN 70064 PPH. Thus, a skilled person can take any individual heterozygous plant (called a "phenotypically superior plant" in Example 2 of US2015/0245570, hereby incorporated by reference in its entirety; pepper variety NUN 70064 PPH is such plant) and generate a combination of parental lines (reverse breeding parental lines) that, when crossed, produce pepper variety NUN 70064 PPH. It is not necessary that the reverse breeding parental lines are identical to the original parental lines. Such breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., pepper variety NUN 70064 PPH), comprising in one aspect: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

In another aspect, the method for producing parental lines for hybrid organisms, e.g., of pepper variety NUN 70064 PPH, which when crossed reconstitute the genome of pepper variety NUN 70064 PPH, comprising:

a. defining a set genetic markers that are present a heterozygous form (H) in a partially heterozygous starting organism;

b. producing at least one further generation from the starting organism by self-pollination (e.g., F2 or F3 generation);

c. selecting at least one pair of progeny organisms in which at least one genetic marker from the set is present in a complementary homozygous form (B vs. A, or A vs. B); and d. optionally repeating steps b) and c) until at least one pair of progeny organisms that have complementary alleles for at least a subset of the genetic markers has been selected as parental lines for a hybrid.

The disclosure also relates to a method of producing a combination of parental lines of a plant of variety NUN 70064 PPH, comprising making doubled haploid cells from haploid cells from said plant or plant part of that plant; and optionally crossing these parental lines to produce and collect seeds. In another aspect, the disclosure relates to a combination of parental lines produced by this method. In still another aspect, the combination of parental lines can be used to produce a seed or plant of variety NUN 70064 PPH, when these parental lines are crossed. In still another aspect, the disclosure relates to a combination of parental lines from which a seed or plant having all physiological and/or morphological characteristics of variety NUN 70064 PPH, e.g., determined at the 5% significance level for numerical characteristics and determined by type or degree for non-numerical characteristics for plants grown under the same conditions.

The disclosure also provides a combination of parental lines which, when crossed, produce a seed or plant having all physiological and/or morphological characteristics of variety NUN 70064 PPH, but one, two, or three which are different (when grown under the same environmental conditions), as well as a seed or plant having all physiological and/or morphological characteristics of variety NUN 70064

PPH, but one, two or three which are different (when grown under the same environmental conditions).

In another aspect, the disclosure provides a method of determining the genotype of a plant of the disclosure comprising detecting in the genome (e.g., a sample of nucleic acids) of the plant at least a first polymorphism or an allele. The skilled person is familiar with many suitable methods of genotyping, detecting a polymorphism or detecting an allele including SNP (Single Nucleotide Polymorphism) genotyping, restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain aspects, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

Also provided is a plant part obtainable from variety NUN 70064 PPH, or from progeny of said variety or from a plant having all but one, two, or three physiological and/or morphological characteristics which are different from those of said variety, or from a vegetatively propagated plant of variety NUN 70064 PPH (or from its progeny or from a plant having all or all but one, two, or three physiological and/or morphological characteristics which are different from those of said variety): a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat, or another maternal tissue which is part of a seed grown on said variety, or a hypocotyl, a cotyledon, a scion, a stock, a rootstock, a pistil, an anther, and a flower or a part thereof.

A part of the plant of pepper variety NUN 70064 PPH (or of progeny of said variety or of a plant having all physiological and/or morphological characteristics but one, two, or three which are different from those of said variety) encompasses any cells, tissues, organs obtainable from the seedlings or plants, such as but not limited to: a pepper fruit or a part thereof, a cutting, a hypocotyl, a cotyledon, seed coat, or pollen. Such plant parts can be stored and/or processed further.

The disclosure further provides for a food or a feed product comprising a part of pepper variety NUN 70064 PPH, or a part of progeny of said variety, or a part of a plant having all but one, two, or three physiological and/or morphological characteristics of NUN 70064 PPH, comprising one or more of such parts, optionally processed (such as canned, chopped, cooked, roasted, in a sauce, in a sandwich, pasted, puréed or concentrated, juiced, frozen, dried, pickled, or powdered). Particularly, the plant part is a pepper fruit or part thereof, and/or an extract from a fruit or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

In another aspect, the disclosure provides for a pepper fruit of variety NUN 70064 PPH, or a part of a fruit of said variety. The fruit can be in any stage of maturity, for example, immature or mature. In another aspect, the disclosure provides for a container comprising or consisting of a plurality of harvested pepper fruits or parts of fruits of said variety, or fruits of progeny thereof, or fruits of a derived variety.

Marketable pepper fruits are generally sorted by size and quality after harvest. Alternatively, the pepper fruits can be sorted by expected shelf life or pungency.

In another aspect, the plant, plant part, or seed of pepper variety NUN 70064 PPH is inside a container, for example, containers such as cans, boxes, crates, bags, cartons, Modified Atmosphere Packaging, films (e.g., biodegradable films), etc. comprising a plant or a part of a plant (fresh and/or processed) or a seed of pepper variety NUN 70064 PPH. In a particular aspect, the container comprises a plurality of seeds, or a plurality of plant parts of pepper variety NUN 70064 PPH. The seed may be disinfected, primed and/or treated with various compounds, such as seed coatings or crop protection compounds. The seed produces a plant of variety NUN 70064 PPH.

Pepper variety NUN 70064 PPH may also be grown for use as rootstocks (stocks) or scions. Typically, different types of peppers are grafted to enhance disease resistance, which is usually conferred by the rootstock, while retaining the horticultural qualities usually conferred by the scion. It is not uncommon for grafting to occur between cultivated pepper varieties and related pepper species. Methods of grafting and vegetative propagation are well-known in the art.

In another aspect, the disclosure relates to a plant comprising a rootstock or scion of pepper variety NUN 70064 PPH.

All documents (e.g., patent publications) are herein incorporated by reference in their entirety, including the following cited references:

Naktuinbow, Calibration book *Capsicum annuum* L., worldwide web at naktuinbow.nl.

UPOV, "Guidelines for the Conduct of Tests for Distinctness, Uniformity and Stability, TG/76/8 (Geneva 2006, revised 2018); world wide web at upov.int/under edocs/tgdocs/en/tg076.pdf.

US Department of Agriculture, Agricultural Marketing Service, "Objective Plant Description of Variety Pepper (*Capsicum* spp.)" world wide web at ams.usda.gov/services/plant-variety-protection/pvpo-c-forms, under pepper.

Hartz, T., et. al, "Bell Pepper Production in California," University of California Division of Agriculture and Natural Resources, Vegetable Production Series, Publication 7217, pp. 1-4.

Ince, A. G., et al., "Genetic Relationship Within and Between *Capsicum* Species", Biochem Genet, 2010, vol. 48, pp. 83-95.

Kothari, S. L., et al., "Chili Peppers—A review on Tissue Culture and Transgenesis", Biotechnology Advances, 2010, vol. 28, pp. 35-48.

Martin, E., et al., "Identification of Markers Linked to Agronomic Traits in Globe Artichoke", Australian Journal of Crop Science, vol. 1, no. 2, pp. 43-46.

Needleman, S. B., et. al., "A General Method Applicable to the Search for Similarities in the Amino Acid Sequence of Two Proteins", Journal of Molecular Biology, 1970, vol. 48(3), pp. 443-53

Nikolova, V., et. al., "Diploidization of Cucumber (*Cucumis sativus* L.) Haploids by Colchini Treatment", Acta Societas Botanicorum Poloniae, 1996, vol. 65, pp. 311-317.

Rice, P., et al., "EMBOSS: The European Molecular Biology Open Software Suite", Trends in Genetics, 2000, vol. 16, Issue 6. pp. 276-277

Sang-Gu, K., et al., "Callus Growth and Plant Regeneration in Diverse Cultivars of Cucumber", Plant Cell, Tissue and Organ Culture, 1988, vol. 12, pp. 67-74

Tiwari, A., et al., "Parthenocarpic Potential in *Capsicum annuum* L. is Enhanced by Carpelloid Structures and Controlled by Single Recessive Gene", BMC Plant Biology, 2011, vol. 11, pp. 2-14, DOI: 10.1186/1471-2229-11-143

Vos, P., et al., AFLP: A New Technique for DNA Fingerprinting 1995, Nucleic Acids Research, 1995, vol. 23, No. 21, pp. 4407-4414.

Wijnker, E., et al., Hybrid Recreation by Reverse breeding in *Arabidopsis thaliana*, Nature Protocols, 2014, vol. 9, pp. 761-772. DOI: doi: 10.1038/nprot.2014.049

U.S. Pat. No. 8,492,619

US2006/0037100

US2015/0245570

US2015/0126380

Development of Pepper Variety NUN 70064 PPH

The hybrid NUN 70064 PPH was developed from a cross between female parental pp 2008 and male parental line pp 1900. Both parental lines are proprietary lines and are not publicly available. The female and male parents were crossed to produce hybrid (F1) seeds of pepper variety NUN 70064 PPH. The seeds of pepper variety NUN 70064 PPH can be grown to produce hybrid plants and parts thereof (e.g., pepper fruit). The hybrid NUN 70064 PPH can be propagated by seeds or vegetatively.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that pepper variety NUN 70064 PPH is uniform and stable.

Deposit Information

A total of 625 seeds of the hybrid variety NUN 70064 PPH was made and accepted according to the Budapest Treaty by Nunhems B.V. on Jan. 6, 2026 at the NCIMB Ltd., Ferguson Building, Craibstone Estate, Bucksburn, Aberdeen AB21 9YA, United Kingdom (NCIMB). The deposit is assigned Accession Number NCIMB 44718. A statement indicating the viability of the sample has been provided. A deposit of pepper variety NUN 70064 PPH and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer and will be replaced if it ever becomes nonviable during that period. Applicant does not waive any rights granted under this patent on this application or under the Plant Variety Protection Act (7 U.S.C. § 2321 et seq.).

Characteristics of Pepper Variety NUN 70064 PPH

The most similar variety to variety NUN 70064 PPH is referred to as Mixteco, a commercial variety from HM Clause.

In Table 1, the characteristics of pepper variety NUN 70064 PPH and the Reference Variety are shown based on a trial under open field conditions in Los Mochis, Northern Sinaloa, Mexico during the trial season August 2021 to April 2022.

In one aspect, the disclosure provides a plant having the physiological and morphological characteristics of pepper variety NUN 70064 PPH as presented in Table 1 when grown under the same environmental conditions, and wherein a representative sample of seed of said pepper variety has been deposited under Accession Number NCIMB 44718.

TABLE 1

Characteristics of Pepper Variety NUN 70064 PPH

| Characteristics | Application Variety (NUN 70064 PPH) | Reference Variety (MIXTECO) |
|---|---|---|
| Seed color: | Yellow | |
| Species: C. annuum C. frutescens C. baccatum C. chinense Other Plant: | *C. annuum* | *C. annuum* |
| Habit: upright/semi-spreading/spreading/other | Upright | Semi-spreading |
| Attitude: erect/semi-erect/prostrate/other | Erect | Semi-erect |
| Basal branches: none/few/many | None | None |
| Branch flexibility: willowy/rigid | Rigid | Rigid |
| Stem strength: weak/intermediate/strong Leaves: | Strong | Strong |
| Mature leaf shape: lanceolate/elliptic | Lanceolate | Lanceolate |
| Leaf color: light green/medium green/dark green/purple/other | Dark green | Dark green |
| Leaf and stem pubescence: absent/light/moderate/heavy | Absent | Absent |
| Margin undulation: absent/very weak/weak/medium/strong/very strong | Absent | absent |
| Blistering: absent/very weak/weak/medium/strong/very strong Fruit: | Absent | absent |
| Fruit group: Bell/Pimiento/Ancho/Cayenne/ Cuban/Jalapeno/Small Hot/Cherry/Short Wax/Long Wax/Tabasco/Habanero | Jalapeño | Jalapeño |
| Immature fruit color: light green/medium green/dark green/very dark green/yellow/purple/ivory/other | Dark green | Dark green |
| Mature fruit color: red/orange/orange-yellow/brown/ivory/green/salmon/ lemon yellow/other | Red | Red |
| Capsaicin in placenta: absent/present | Present | Present |
| Pungency: sweet/hot | Hot | Hot |
| Fruit flavor: mild pepper flavor/moderate pepper flavor/strong pepper flavor/other | Other | Other |
| Fruit glossiness: dull/moderate/shiny | Shiny | Shiny |
| Surface smoothness: smooth/rough | Smooth | Smooth |
| Fruit position: upright/horizontal/pendant | Pendant | Pendant |
| Calyx shape: cup-shaped/saucer-shaped | Saucer-shape | Saucer-shape |

TABLE 1-continued

Characteristics of Pepper Variety NUN 70064 PPH

| Characteristics | Application Variety (NUN 70064 PPH) | Reference Variety (MIXTECO) |
|---|---|---|
| Fruit base shape: cupped/rounded | Rounded | Rounded |
| Fruit apex shape: pointed, blunt | Pointed | Pointed |
| Fruit shape: bell/conical/elongate/oblong/oblate/globe/other | Elongate | Elongated |
| Fruit shape longitudinal section: flattened/round/heart-shaped/square/rectangular/trapezoid/narrow triangular/triangular/horn-shaped | Trapezoid | Trapezoid |
| Fruit shape cross section: elliptic/triangular/quadrangular/circular | Circular | Circular |
| Fruit set: scattered/concentrated | Scattered | Concentrated |
| Interloculary grooves: absent/very shallow/shallow/medium/deep/very deep | Absent | Absent |
| Number of locules: predominantly two/equally two and three/predominantly three/equally three and four/predominantly four and more | Predominantly three | Predominantly three |
| Pedicel shape: straight/curved | Straight | Straight |
| Pedicel cavity: absent/present | Absent | Absent |
| Maturity: | | |
| Time of maturity: Very early/early/medium/late/very late | Medium | Medium |
| Disease resistances: | | |
| Tomabovirus (Tobacco Mosaic Virus) Pathotype 0: | Resistant | Resistant |
| Tomato Spotted Wilt Virus (TSWV) | Susceptible | Susceptible |
| Xanthomonas campestris pv. Vesicatoria, Pathotype 1 | Resistant | Resistant |

The invention claimed is:

1. A plant, plant part, or seed of pepper variety NUN 70064 PPH, wherein a representative sample of seed of said pepper variety is deposited under Accession Number NCIMB 44718.

2. A plant part of the plant of claim 1, wherein said plant part is a fruit, a leaf, pollen, an ovule, a cell, a scion, a root, a rootstock, a cutting, or a flower.

3. A seed that produces the plant of claim 1.

4. A pepper plant having all the physiological and morphological characteristics of the plant of claim 1 when grown under the same environmental conditions.

5. A tissue culture or cell culture of regenerable cells of the plant or plant part of claim 1.

6. The tissue or cell culture according to claim 5, comprising cells or protoplasts obtained from a plant part suitable for vegetative reproduction, wherein the plant part is a meristem, a cotyledon, a hypocotyl, a pollen, a leaf, an anther, a root, a root tip, a pistil, a petiole, a flower, a fruit, a seed, a stem, or a stalk.

7. A method of producing the plant of claim 1, or a part thereof, said method comprising vegetative propagation of at least a part of pepper variety NUN 70064 PPH, wherein a representative sample of seed of said pepper variety is deposited under Accession Number NCIMB 44718.

8. The method of claim 7, wherein said part is a cutting, a cell culture, or a tissue culture.

9. A vegetatively propagated plant, or part thereof, produced by the method of claim 7, wherein the plant, or part thereof has all of the physiological and morphological characteristics of the plant of variety NUN 70064 PPH when grown under the same environmental conditions, wherein a representative sample of seed of said pepper variety is deposited under Accession Number NCIMB 44718.

10. A method of producing a pepper plant, said method comprising crossing the plant of claim 1 with itself or a second pepper plant, selecting a progeny pepper plant from said crossing, allowing the progeny pepper plant to form seed, wherein a representative sample of seed of said pepper variety NUN 70064 PPH is deposited under Accession Number NCIMB 44718.

11. A method of introducing a desired trait into the plant of claim 1, comprising transforming the plant of pepper variety NUN 70064 PPH with a transgene that confers the desired trait, wherein the plant comprises the desired trait and otherwise has all of the physiological and morphological characteristics of the plant of pepper variety NUN 70064 PPH.

12. A pepper plant produced by the method of claim 11, wherein the transformed plant otherwise comprises the desired trait and otherwise has all the physiological and morphological characteristics of pepper variety NUN 70064 PPH.

13. A method of making doubled haploid cells of the plant of claim 1, said method comprising making double haploid cells from haploid cells of the plant or seed of pepper variety NUN 70064 PPH, wherein a representative sample of seed of said pepper variety is deposited under Accession Number NCIMB 44718.

14. A plant comprising the scion or rootstock of claim 2.

15. A container comprising the plant or seed of claim 1.

16. A food or feed product or a processed product comprising the plant part of claim 2, wherein said plant part comprises at least a regenerable cell of pepper variety NUN 70064 PPH.

17. A method of introducing a single locus conversion into the plant of claim 1, said method comprising:

a. crossing the plant of claim 1 with a second pepper plant comprising a desired single locus conversion to produce F1 progeny plants;

b. selecting F1 progeny plants that have the single locus conversion to produce selected F1 progeny plants;

c. crossing the selected F1 progeny plants with pepper variety NUN 70064 PPH to produce backcross progeny plants;

d. selecting backcross progeny plants that have the single locus conversion and otherwise comprise all of the physiological and morphological characteristics of pepper variety NUN 70064 PPH to produce selected backcross progeny plants; and e. repeating steps (c) and (d) one or more times in succession to produce selected second or higher backcross progeny plants that comprise the single locus conversion and otherwise comprise all of the physiological and morphological characteristics of the plant of pepper variety NUN 70064 PPH, wherein a representative sample of seed of said pepper variety is deposited under Accession Number NCIMB 44718.

18. A pepper plant produced by the method of claim 17, wherein the plant comprises the single locus conversion and otherwise has all the physiological and morphological characteristics of pepper variety NUN 70064 PPH, and wherein the single locus confers male sterility, herbicide tolerance, insect resistance, pest resistance, disease resistance, environmental stress tolerance, modified carbohydrate metabolism, or modified protein metabolism.

19. A method of producing a modified pepper plant, said method comprising mutating a target gene by targeted gene editing in a pepper plant or plant part of pepper variety NUN 70064 PPH, wherein a representative sample of seed of said pepper variety is deposited under Accession Number NCIMB 44718, wherein the target gene modifies a desired trait and wherein the desired trait is male sterility, herbicide tolerance, insect resistance, pest resistance, disease resistance, environmental stress tolerance, modified carbohydrate metabolism, or modified protein metabolism.

20. A pepper plant produced by the method of claim 19.

21. A method for determining the genotype of the plant of claim 1, said method comprising obtaining a sample of nucleic acids from said plant and detecting in said nucleic acids a plurality of polymorphisms, thereby determining the genotype of the plant, and storing the results of detecting the plurality of polymorphisms on a computer readable medium.

22. A method of producing a pepper fruit, said method comprising growing the plant of claim 1 until it develops at least a leaf or head, and collecting the leaf or head.

23. The fruit produced by the method of claim 22.

24. A container comprising the fruit produced by the method of claim 23.

25. A method for developing a pepper plant in a pepper breeding program, said method comprising applying plant breeding techniques comprising recurrent selection, backcrossing, pedigree breeding, mass selection, mutation breeding, genetic marker enhanced selection, or genetic transformation to the plant of claim 1 or part thereof, wherein said plant breeding techniques result in a development of a pepper plant.

26. A method of producing a pepper plant derived from the plant of claim 1, said method comprising:

a. preparing a progeny pepper plant derived from pepper variety NUN 70064 PPH by crossing the plant of pepper variety NUN 70064 PPH with itself or with a second pepper plant, wherein a representative sample of seed of said pepper variety has been deposited under Accession Number NCIMB 44718;

b. crossing the progeny plant with itself or a second pepper plant to produce seed of a progeny plant of the subsequent generation;

c. growing a progeny plant of the subsequent generation from said seed and crossing the progeny plant of the subsequent generation with itself or a second pepper plant; and d. repeating step (b) and (c) for at least one more generation to produce a pepper plant derived from pepper variety NUN 70064 PPH.

27. A method of producing a pepper seed, said method comprising crossing pepper plants and harvesting the resultant seed, wherein at least one pepper plant is the plant of claim 1, wherein a representative sample of seed of said pepper variety NUN 70064 PPH is deposited under Accession Number NCIMB 44718.

* * * * *